United States Patent
Pye et al.

(10) Patent No.: US 9,156,847 B2
(45) Date of Patent: Oct. 13, 2015

(54) PROCESSES AND INTERMEDIATES FOR PREPARING A MEDICAMENT

(71) Applicant: Janssen Pharmaceutica NV, Beerse (BE)

(72) Inventors: Philip Pye, Beerse (BE); Cyril Ben Haim, Beerse (BE); Matteo Conza, Schaffhausen (CH); Ioannis Nicolaos Houpis, Antwerp (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/203,622

(22) Filed: Mar. 11, 2014

(65) Prior Publication Data

US 2014/0275126 A1    Sep. 18, 2014

Related U.S. Application Data

(60) Provisional application No. 61/786,842, filed on Mar. 15, 2013.

(51) Int. Cl.

| C07D 487/04 | (2006.01) |
|---|---|
| C07D 401/04 | (2006.01) |
| A61K 31/519 | (2006.01) |
| C07D 211/56 | (2006.01) |

(52) U.S. Cl.
CPC ............ *C07D 487/04* (2013.01); *C07D 211/56* (2013.01); *C07D 401/04* (2013.01)

(58) Field of Classification Search
CPC .. C07D 487/04; C07D 401/04; C07D 211/56; A61K 31/519
USPC .......... 546/211, 244; 544/262; 514/334, 262.1
See application file for complete search history.

(56) References Cited

U.S. PATENT DOCUMENTS

| 7,514,444 | B2 * | 4/2009 | Honigberg et al. | ...... 514/263.22 |
|---|---|---|---|---|
| 8,623,879 | B2 * | 1/2014 | Giovannini et al. | ....... 514/262.1 |
| 2011/0082137 | A1 * | 4/2011 | Giovannini et al. | ....... 514/234.2 |
| 2014/0079690 | A1 * | 3/2014 | Buggy et al. | ............... 424/133.1 |

FOREIGN PATENT DOCUMENTS

| WO | WO 2008/039218 A2 | 4/2008 |
|---|---|---|
| WO | WO 2014004707 A1 * | 1/2014 |
| WO | WO 2014068527 A1 * | 5/2014 |
| WO | WO 2014082598 A1 * | 6/2014 |

OTHER PUBLICATIONS

Horwood et al., "Bruton's Tyrosine Kinase Is Required for Lipopolysaccharide-induced Tumor Necrosis Factor α Production.", *The Journal of Experimental Medicine*, Jun. 16, 2003, pp. 1603-1611, vol. 197(12).
Iwaki et al., "Btk Plays a Crucial Role in the Amplification of Fc RI-mediated Mast Cell Activation by Kit*.", Journal of Biological Chemistry, Dec. 2, 2005, pp. 40261-40270, vol. 280(48).
Jeffries et al., "Bruton's Tyrosine Kinase Is a Toll/Interleukin-1 Receptor Domain-binding Protein That Participates in Nuclear Factor B Activation by Toll-like Receptor 4*.", Journal of Biological Chemistry, 2003, pp. 26258-26264, vol. 278(28).
Kurosaki, T., "Functional dissection of BCR signaling pathways.", *Curr. Op. Imm.*, 2000, pp. 276-281.
Schaeffer, E.M. and Schwartzberg, P.L., "Tec family kinases in lymphocyte signaling and function.", *Curr. Op. Imm.* 2000, pp. 282-288.
Vassilev et al., "Bruton's Tyrosine Kinase as an Inhibitor of the Fas/CD95 Death-inducing Signaling Complex*.", *Journal of Biological Chemistry*, 1999, pp. 1646-1656, vol. 274(3).

* cited by examiner

*Primary Examiner* — Venkataraman Balasubramanian

(57) ABSTRACT

Disclosed is a process for the preparation of the following compounds:

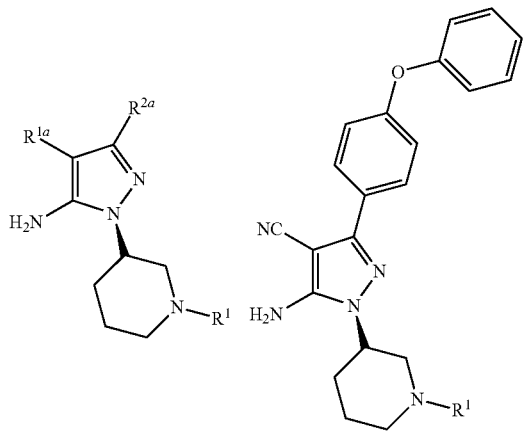

where $R^1$, $R^{1a}$ and $R^{2a}$ have the definitions in the description, as well as a process to prepare other intermediates that may be useful to synthesize downstream products, especially compounds that are useful as medicaments, for instance Bruton's tyrosine kinase (Btk) inhibitors such as ibrutinib. Also disclosed are other processes, other intermediates and compounds per se.

16 Claims, No Drawings

PROCESSES AND INTERMEDIATES FOR PREPARING A MEDICAMENT

CROSS REFERENCE TO RELATED APPLICATIONS

This application claims the benefit of U.S. Provisional Application 61/786,842 filed on Mar. 14, 2013, which is incorporated by reference herein in its entirety.

FIELD OF THE INVENTION

The present invention relates to synthesis procedures and synthesis intermediates of substituted bicyclic compounds, especially compounds that are useful as medicaments, for instance Bruton's tyrosine kinase (Btk) inhibitors such as ibrutinib.

BACKGROUND OF THE INVENTION

Ibrutinib is an organic small molecule having IUPAC name 1-[(3R)-3-[4-amino-3-(4-phenoxyphenyl)pyrazolo[3,4-d]pyrimidin-1-yl]piperidin-1-yl]prop-2-en-1-one. It is described in a number of published documents, including international patent application WO 2008/039218 (Example 1b), and is described as an irreversible inhibitor of Btk.

Btk plays an essential role in the B-cell signaling pathway linking cell surface B-cell receptor stimulation to downstream intracellular responses. Btk is a key regulator of B-cell development, activation, signaling, and survival (Kurosaki, *Curr Op Imm,* 2000, 276-281; Schaeffer and Schwartzberg, *Curr Op Imm* 2000, 282-288). In addition, Btk plays a role in a number of other hematopoetic cell signaling pathways, e.g. Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See e.g., C. A. Jeffries, et al., (2003), *Journal of Biological Chemistry* 278:26258-26264; N. J. Horwood, et al., (2003), *The Journal of Experimental Medicine* 197:1603-1611; Iwaki et al. (2005), *Journal of Biological Chemistry* 280(48):40261-40270; Vassilev et al. (1999), *Journal of Biological Chemistry* 274(3):1646-1656, and Quek et al (1998), *Current Biology* 8(20):1137-1140.

Ibrutinib is therefore being studied in Phase II and III clinical trials for various hematological malignancies such as chronic lymphocytic leukemia, mantle cell lymphoma, diffuse large B-cell lymphoma and multiple myeloma.

There are various processes for preparing functionalised bicyclic heterocycles, for example as described in US patent document US 2011/0082137, which includes syntheses to fused bicycles from pyrazoles and substituted hydrazines.

Ibrutinib may be prepared in WO 2008/039218 (Example 1b) in accordance with the following scheme:

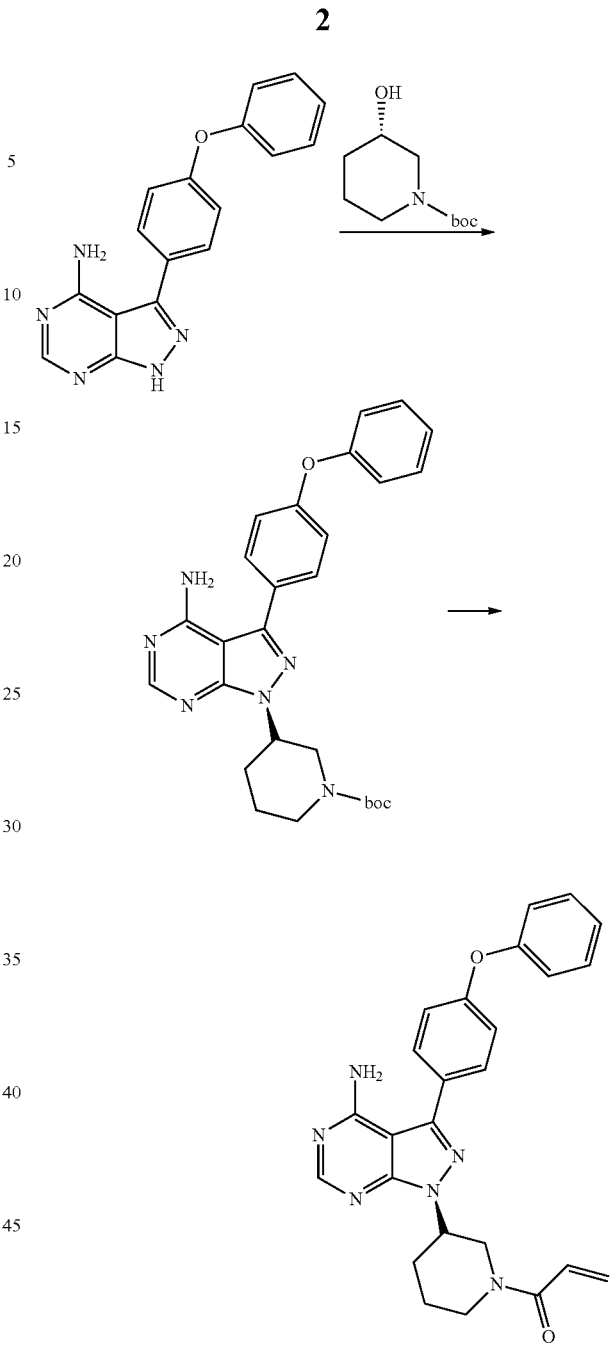

First, 4-amino-3-(4-phenoxyphenyl)-1H-pyrazole[3,4-d]pyrimidine may be prepared in accordance with procedures described in WO 2008/039218, for instance by converting 4-phenoxybenzoic acid to the corresponding acyl chloride (by using thionyl chloride), which latter product may be reacted with malononitrile to prepare 1,1-dicyano-2-hydroxy-2-(4-phenoxyphenyl)ethene. The methoxy moiety is then methylated using trimethylsilyldiazomethane, and that methylated product is the treated with hydrazine hydrate to provide 3-amino-4-cyano-5-(4-phenoxyphenyl)pyrazole, which is reacted with formamide to provide 4-amino-3-(4-phenoxyphenyl)-1H-pyrazole[3,4-d]pyrimidine, as illustrated in the following scheme:

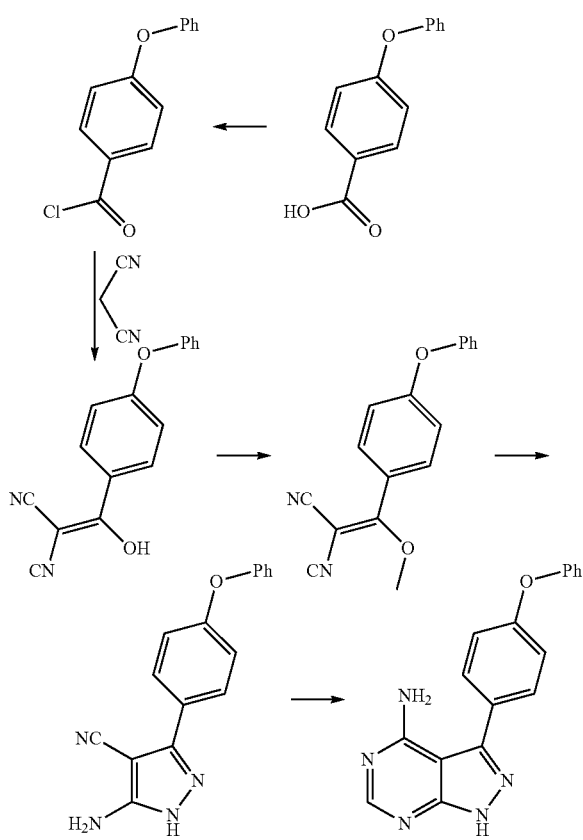

Thereafter, the 4-amino-3-(4-phenoxyphenyl)-1H-pyrazole[3,4-d]pyrimidine may have the requisite piperidinyl moiety introduced at the 1H-position (i.e. on the —NH of the pyrazole moiety). As indicated in the above scheme, this is done by means of a Mitsunobu reaction—more specifically by converting the hydroxy moiety of the Boc-protected 3-hydroxypiperidine-1-carboxylate to a better leaving group, thereby allowing a substitution reaction with the —NH moiety of the pyrazole (with inversion). Hence, the chirality of the hydroxypiperidine is translated into the product, which is then converted to the single enantiomer ibrutinib by Boc-deprotection and acylation with acryl chloride.

This process has a number of disadvantages, such as those associated with cost, efficiency and environmental disadvantages. For instance the Mitsunobu step may be wasteful, costly and cumbersome. It is therefore desired to find a new process that overcomes these disadvantages.

There is now provided a process for the preparation of a compound of formula I, (I)

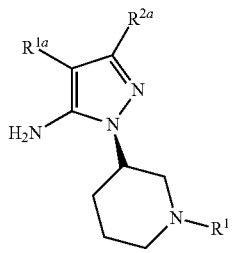

or a derivative thereof, wherein
$R^1$ represents a nitrogen protecting group;
$R^{1a}$ represents —CN, —C(O)OR$^{1b}$ or —C(O)N(R$^{1c}$)(R$^{1d}$);
$R^{1b}$, $R^{1c}$ and $R^{1d}$ each independently represent $C_{1-6}$ alkyl, aryl or heteroaryl;
$R^{2a}$ represents:
(i) phenyl substituted at the 4-position with halo or —O—R$^{2b}$; or
(ii) hydrogen;
$R^{2b}$ represents hydrogen or phenyl;
which process comprises reaction of a compound of formula II, (II)

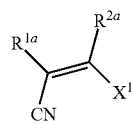

or a derivative thereof, wherein
$R^{1a}$ and $R^{2a}$ are as defined above;
$X^1$ represents a suitable leaving group,
with a compound of formula III, (III)

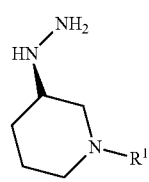

or a derivative thereof, wherein $R^1$ is as defined above,
which process is hereinafter referred to as a "process of the invention".

In the processes of the invention described herein, it is indicated that "derivatives" may be employed, which includes salts and solvates. Hence, for instance the compound of formula (III), i.e. the hydrazine, may be in the form of the free base or in the form of a salt (e.g. a di-hydrogen chloride salt, although the hydrazine may be in another salt form). Where appropriate, "derivative" may also encompass a relevant protecting group (which may be removed later in the synthesis scheme). It should also be noted that compounds mentioned herein may exhibit isomerism, e.g. tautomerism.

It is further indicated above that $R^1$ is a nitrogen protecting group. Such groups include those that result in the formation of:
  an amide (e.g. N-acetyl)
  optionally substituted N-alkyl (e.g. N-allyl or optionally substituted N-benzyl)
  N-sulfonyl (e.g. optionally substituted N-benzenesulfonyl)
  a carbamate
  a urea
  trityl (triphenylmethyl), diphenylmethyl, or the like
Hence, $R^1$ may, amongst other groups, represent:
  —C(O)R$^{t1}$ (in which R$^{t1}$ preferably represents $C_{1-6}$ alkyl or optionally substituted aryl);
  $C_{1-6}$ alkyl, which alkyl group is optionally substituted by one or more substituents selected from optionally substituted aryl (e.g. preferably forming a benzyl moiety);

—S(O)₂R^{r2} (in which R^{r2} preferably represents optionally substituted aryl); or, preferably, —C(O)OR^{r3} (in which R^{r3} preferably represents optionally substituted aryl or, more preferably, optionally substituted $C_{1-6}$ (e.g. $C_{1-4}$ alkyl, e.g. tert-butyl (so forming, for example, a tert-butoxycarbonyl protecting group, i.e. when taken together with the amino moiety, a tert-butylcarbamate group) or a —CH₂phenyl group (so forming a carboxybenzyl protecting group);

—C(O)N(R^{r4})R^{r5} (in which, preferably, R^{r4} and R^{r5} independently represent hydrogen, $C_{1-6}$ alkyl, optionally substituted aryl or —C(O) R^{r6}, and R^{r6} represents $C_{1-6}$ alkyl or optionally substituted aryl).

Unless otherwise specified, alkyl groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated.

The term "aryl", when used herein, includes $C_{6-10}$ groups. Such groups may be monocyclic, bicyclic or tricyclic and, when polycyclic, be either wholly or partly aromatic. $C_{6-10}$ aryl groups that may be mentioned include phenyl, naphthyl, and the like. For the avoidance of doubt, the point of attachment of substituents on aryl groups may be via any carbon atom of the ring system.

The term "heteroaryl", when used herein, includes 5- to 14-membered heteroaryl groups containing one or more heteroatoms selected from oxygen, nitrogen and/or sulfur. Such heteroaryl group may comprise one, two or three rings, of which at least one is aromatic. Preferably, such groups are 5- to 12-membered, e.g. 5- to 10-membered.

Where mentioned herein, $C_{1-6}$ alkyl, aryl and heteroaryl may be optionally substituted. Such substitution is possible if it does not affect the concept of the invention, i.e. the process(es) defined herein (which may be performed on certain compounds irrespective of the substitution pattern thereon). Such substituents include aryl (e.g. phenyl, itself optionally substituted by substituents selected from halo, alkyl and the like), alkyl, halo, —CN and the like.

It is indicated that X¹ represents a suitable leaving group, and in particular may represent chloro, bromo, iodo, —OR^{3a} (in which R^{3a} represents optionally substituted alkyl, e.g. in which the optional substituent(s) include aryl such as phenyl, so forming e.g. —OCH₃, —OCH₂-phenyl or the like) or a sulfonate group (e.g. —O—S(O)₂R^{4a}, in which R^{4a} represents optionally substituted alkyl or aryl, so forming e.g. —OS(O)₂CF₃, —OS(O)₂CH₃ or —S(O)₂PhMe or the like, i.e. tosyl, mesyl or the like).

Preferred compounds of formula (I) that may be prepared by a process of the invention described herein include those in which:

R^{1a} represents —CN;

R^{2a} represents phenyl substituted at the 4-position by —O—R^{2b}; and/or

R^{2b} represents phenyl;

hence the compound of formula (I) is preferably:

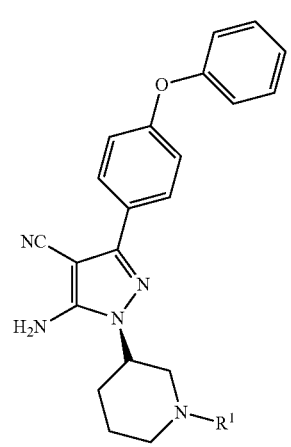

(I)

the compound of formula (II) is preferably:

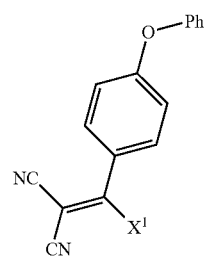

(II)

wherein, preferably, X¹ represents —OR^{3a}, in which R^{3a} is preferably alkyl, more preferably unsubstituted alkyl and, most preferably, methyl, so forming a —OCH₃ group;

and hence, most preferably, the compound of formula (II) represents:

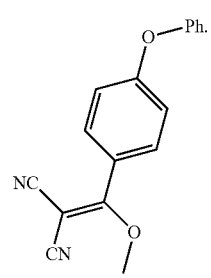

(II)

For the avoidance of doubt, the compound of formula (III) is a single enantiomer containing a chiral centre that has an (R)-configuration. By single enantiomer, we mean that the compound is present in some enantiomeric excess (in this case, that there is more (R)-enantiomer present than the (S)-enantiomer), for instance in greater than 50% ee, e.g. greater than 60% ee. The chirality is retained in the process of the reaction, i.e. the reaction is stereospecific, and the compound of formula (I) thereby produced is also a single enantiomer with the same configuration at the relevant chiral centre. Downstream synthetic steps will also proceed with retention of the stereochemistry (unless specified otherwise).

Particularly preferred protecting groups that $R^1$ may represent include those forming carbamates (especially the tert-butoxycarbonyl or t-Boc group and the carboxybenzyl or Cbz group) and substituted alkyl moieties (especially the benzyl group). Such protecting groups may be more easily introduced onto the compound of formula (III) and/or ultimately more easily removed from the relevant nitrogen atom in a downstream step.

Such a process of the invention may be conducted using the free base of a compound of formula (III) or salt thereof, e.g. a di-hydrogen chloride salt of the compound of formula (III). Further the protecting group $R^1$ is preferably a non acid-labile protecting group (e.g. a group labile to base or removable though hydrogenation or the like) such as a carboxybenzyl (Cbz) protecting group. However, the choice of this protecting group is influenced by the choice of the protecting group $R^2$ (e.g. the two are preferably mutually compatible) as indicated hereinafter.

In this aspect of the process of the invention, the compound of formula (III) (or derivative thereof, e.g. di-HCl salt) may be added to the compounds of formula (II). Preferably less than two equivalents of the compound of formula (III) is employed compared to the compound of formula (II), more preferably less than 1.5 equivalents. However, the equivalents ratio of compound of formula (III) to compound of formula (II) may be between 1.5:1 to 1:1.5, preferably between 1.2:1 to 1:1.2 and in particular, the ratio is about 1:1.

Preferably, this aspect of the process of the invention may be performed in a suitable solvent, such as in the presence of a polar solvent, such as an alcoholic solvent (e.g. ethanol) and/or water, or mixtures thereof. It is preferred that a mixture of an alcohol (e.g. ethanol) and water is employed. Compared to the weight of the compound of formula (II) employed, at least one (e.g. at least five, but preferably less than 20) volume equivalent(s) of the solvent/alcohol and at least one (e.g. at least five, but preferably less than 20) volume equivalents of water are employed. Preferably about 13 volume equivalents of the alcohol and about 10 volume equivalents of water are employed.

Preferably, the compound of formula (II) in the presence of a suitable solvent (as described above) is cooled to below room temperature, for example to below 10° C., e.g. to about 5° C. The compound of formula (III) (or derivative thereof) is then added to the mixture of compound of formula (II) and solvent. Preferably this is done so as to maintain the temperature of the reaction mixture below room temperature (e.g. at below about 10° C., preferably between 5 and 10° C.). For instance, this addition may be drop-wise.

This process aspect of the invention is preferably conducted in the presence of a base, such as an organic base, preferably an amine base such as a tertiary amine base (e.g. triethylamine). Preferably between one and four molar equivalents of base are employed in the process of the invention (compared to the molar equivalents of the compound of formula (II) or (III)), and more preferably between 1.5 and 2.5 equivalents are employed (e.g. about two equivalents). Preferably the base is added dropwise, and preferably the temperature is maintained at below room temperature (e.g. at below about 10° C., preferably between 5 and 10° C.).

After the addition of the base, the reaction mixture is the preferably allowed to warm to about room temperature, after which it is allowed to stir at that temperature for a period of time (during which the conversion to desired product compound (I) may be monitored), which may depend on the conversion rate to product. Typically, the reaction mixture is allowed to stir for at least 20 minutes, for example for about one hour, after which further water may be added (e.g. between about 10 and 20 volume equivalents), the reaction mixture may be cooled (again) to below room temperature (e.g. to below about 10° C., preferably about 5° C. or below, e.g. about 0° C.). The desired product may then solidify, and may therefore be separated/isolated by filtration. It may be further purified if required.

Such an aspect of the process of the invention has several advantages. For instance, the fact that the substituted hydrazine of formula (III) (that may be employed in e.g. the free base form, or in the salt form which may be formed in situ) is employed in the reaction has at least the following advantages:

(i) the use of hydrazine hydrate is avoided, which is a hazardous reagent to handle, especially at high temperatures (for instance hydrazine is combustible even in the absence of oxygen);

(ii) the reaction leads to a 1N-substituted pyrazole and hence downstream substitution at the 1N-position is circumvented (when substitution is required at that position), for instance a downstream Mitsunobu reaction to introduce a substituent is circumvented, the latter reaction generating enormous amounts of waste (e.g. the Mitsunobu reaction may require two equivalents of the 3-hydroxy-N-Boc piperidine, due to a competing elimination reaction);

(iii) the use of the expensive chiral 3-hydroxy-N-Boc piperidine is circumvented;

(iv) the reaction of compound (II) with a non-symmetrical hydrazine may be expected to result in a variety of products (as opposed to reaction with the symmetrical hydrazine itself) but however, advantageously and unexpectedly, the reaction proceeds in a regioselective manner. That is the process of the invention predominantly results in the formation of a pyrazole with a substitution pattern as depicted by the compound of formula (I), i.e. in the 1(N)-position the piperidine, $R^{2a}$ group (e.g. 4-phenoxy-phenyl) in the 3-position, etc, as opposed to a pyrazole with the piperidine at the 2-position adjacent the $R^{2a}$ group. Advantageously, the desired regioisomer is present in higher quantity than the undesired regioisomer, and for instance is present in a ratio of greater than 75:25 compared to the undesired regioisomer, more particularly, this ratio is greater than 90:10, and most advantageously there may be a negligible or undetectable amount of the undesired regioisomer.

Hence, this aspect of the process of the invention may be advantageous in terms of economy (e.g. cost of goods), efficiency and environmental considerations (e.g. less waste).

After the first process of the invention, the compound of formula (I) that is prepared may be converted to a compound of formula (IV),

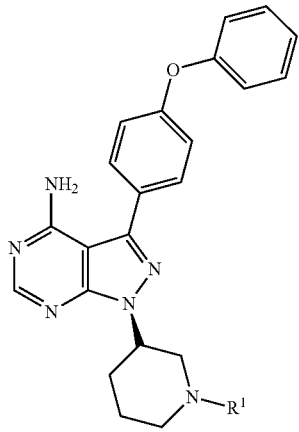

(IV)

or a derivative (including isomer) thereof, wherein R$^1$ is as hereinbefore defined.

In the conversion to the compound of formula (IV), the compound of formula (I) may first be converted to a compound of formula (IVA),

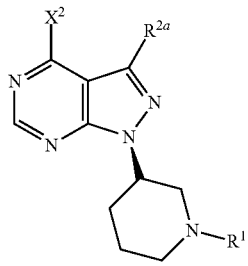

(IVA)

or a derivative (including isomer), wherein X$^2$ represent —OH or —NH$_2$, and R$^1$ and R$^{2a}$ are as hereinbefore defined.

For instance, for compounds of formula (I) in which R$^{1a}$ represents —CN, a corresponding product of formula (IVA) in which X$^2$ represents —NH$_2$ may be produced by reaction with either:

(i) formamide (HCONH$_2$);
(ii) formamidine or a formamidine salt H—C(=NH)— NH$_3$$^+$X$^-$, wherein X$^-$ represents a suitable counterion, such as a halide (e.g. Cl$^-$) or an oxy anion (e.g. acyl-O$^-$), so forming for example formamidine HCl or formamidine acetate or the like;
(iii) alkyl (e.g. ethyl) formimidate, or a salt thereof, such as ethyl formimidate HCl;
(iv) ethylorthoformate followed by ammonium acetate.

For compounds of formula (I) in which R$^{1a}$ represents —C(O)OR$^{1b}$ or —C(O)N(R$^{1c}$)(R$^{1d}$), a corresponding product of formula (IVA) in which X$^2$ represents —OH (or a tautomer thereof, as depicted by formula (IVB) below) may be produced by reaction with for example, CH(OEt)$_3$ optionally in the presence of a catalyst (e.g. ZnCl$_2$, 0.1 equiv), followed by the addition of e.g. NH$_4$OAc, which reaction may be performed in the presence of a suitable solvent (e.g. an aromatic solvent such as toluene):

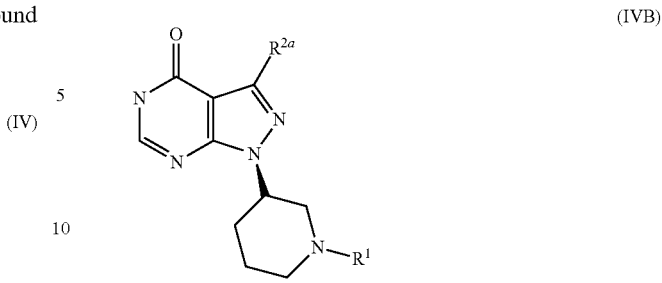

(IVB)

Thereafter, compounds of formula (IVA) in which X$^2$ represents —OH (or the tautomer, i.e. compound (IVB) depicted above) may be converted to corresponding compounds of formula (IVA) in which X$^2$ represents —NH$_2$, by first converting to the corresponding chlorinated derivative (which need not be isolated) followed by a nucelophilic aromatic substitution to provide the desired compound, conditions including the use of POCl$_3$ (or another suitable chlorinating reagent) followed by reaction with NH$_4$OAc (or another suitable source of ammonia).

For compounds of formula (IVA) in which R$^{2a}$ represents hydrogen, such a compound may be converted to a compound of formula (IVC):

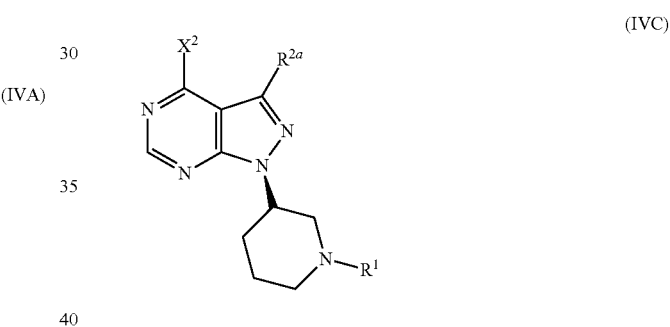

(IVC)

wherein X$^2$ is as hereinbefore defined, and X$^3$ is a suitable group such as halo (e.g. bromo, chloro or preferably, iodo), which reaction may take place in the presence of a source of halide, for instance an electrophile that provides a source of iodine includes iodine, diiodoethane, or preferably, N-iodosuccinimide, and sources of bromide and chloride include N-bromosuccinimide and N-chlorosuccinimide, and which reaction may be performed in the presence of a suitable solvent such as an alcohol (e.g. methanol) or preferably a halogenated solvent (e.g. chloroform) or a polar aprotic solvent (such as DMF).

Compounds of formula (IVC), in particular those in which X$^2$ represents —NH$_2$, may be converted to compounds of formula (IVA) in which R$^{2a}$ represents phenyl substituted at the 4-position with halo or —OR$^{2b}$, by reaction of the compound of formula (IVC) with a compound of formula (IVD):

X$^4$—R$^{2aa}$ (IVD)

wherein R$^{2aa}$ represents phenyl substituted at the 4-position with halo or —OR$^{2b}$ (with R$^{2b}$ as hereinbefore defined), and wherein X$^4$ represents a suitable group such as —B(OH)$_2$, —B(OR$^w$)$_2$ or —Sn(R$^w$)$_3$, in which each R$^w$ independently represents a C$_{1-6}$ alkyl group, or, in the case of —B(OR$^w$)$_2$, the respective R$^w$ groups may be linked together to form a 4- to 6-membered cyclic group (such as a 4,4,5,5-tetramethyl-1,3,2-dioxaborolan-2-yl group, thereby forming e.g. a pinacolato boronate group), and wherein the coupling reaction may be performed in the presence of a suitable catalyst system, e.g. a metal (or a salt or complex thereof) such as Pd, CuI, Pd/C, Pd(OAc)$_2$, Pd(Ph$_3$P)$_2$Cl$_2$, Pd(Ph$_3$P)$_4$, Pd$_2$(dba)$_3$ and/or NiCl$_2$ (preferred catalysts include palladium) and a ligand such as PdCl$_2$(dppf).DCM, t-Bu$_3$P or the like, optionally in the presence of a suitable base (e.g. a carbonate base, hydroxide base, etc) and a suitable solvent.

Where, e.g. for compounds of formula (IVA) as defined above in which X$^2$ represents —NH$_2$ (or a protected derivative thereof) and R$^{2a}$ represents phenyl substituted at the 4-positon by halo or —OH, then conversion to the compound of formula (IV) may be possible by a coupling reaction with X$^4$-phenyl-O-phenyl or X$^4$-phenyl, for instance using similar catalytic coupling reactions to those mentioned above.

Hence, ultimately compounds of formula (IV) may be prepared according to the processes mentioned above.

The processes discussed above (including those to prepare compounds of formula (IV) and (IVA)) are also embraced by the concept of the invention, and are also processes that may be referred to herein as a "process of the invention".

There is therefore provided a process for the preparation of a compound of formula (IV) which process comprises a process for the preparation of a compound of formula (I) as hereinbefore defined followed by a process for the conversion of (I) to (IV) as hereinbefore described.

There is also provided a process for the preparation of a compound (IV) or (IVA), which process comprises reaction of a compound of formula (I) (as hereinbefore defined) with a formamidine salt defined at (ii) above. Such a process is also an aspect of the invention and has associated advantages compared with reaction with formamide. For instance, the use of the formamidine salt may be advantageous as it circumvents the use of formamide, the latter being using in prior processes at high temperatures (e.g. at about 165° C., which represents a thermal hazard), whereas the use of the formamidine salt allows lower temperatures to be employed.

This aspect of the invention (conversion of compound (I) to compound (IV) or (IVA)) is preferably performed by reaction of the compound (I) with a formamidine salt (as defined hereinbefore). The formamidine salt is preferably an acetate salt and is preferably employed in excess compared with the molar equivalents of compound of formula (I) employed (e.g. in greater than two equivalents compared to compound of formula (I), e.g. greater than five equivalents, such as greater than 10 equivalents and preferably about fifteen equivalents).

This aspect of the process of the invention may be performed in the presence of a suitable solvent, which may be selected from aromatic solvents (e.g. toluene), alcohols, ethers and N-methyl-2-pyrrolidone, or the like. Glycols ethers may be particularly preferred (e.g. due to high boiling points), and a particularly preferred solvent is therefore ethylene glycol monoethyl ether. The solvent is preferably degassed and the reaction is preferably carried out under an inert atmosphere. More than five volume equivalents of solvent is employed (e.g. more than ten, and preferably around 13).

The resultant reaction mixture is then preferably heated to above room temperature, e.g. to above 40° C., e.g. above 60° C. such as above 80° C. Most preferably it is heated to above 100° C. However, the temperature of the reaction mixture is preferably below 160° C., for instance the preferred temperature range is between 100° C. and 140° C., most preferably between about 110° C. and 130° C. (e.g. about 120° C.).

The reaction mixture may be monitored for progress, consequently affecting the time period of the reaction. After adequate completion of the reaction, mixture may be allowed to cool down and the reaction mixture worked up to provided the desired compound.

There is further provided a process for the preparation of a compound of formula (III) as hereinbefore defined, which process comprises resolution of a corresponding racemic mixture (or derivative, e.g. protected derivative, thereof), which may be performed by means of chiral chromatography (e.g. using chiral SFC), thereby advantageously obtaining a compound of formula (III) in greater than 50% ee, for example greater than 60% ee. Given that the process of the invention is stereoselective, it is possible to purify downstream so as to provide an enantiomerically pure downstream compound.

Advantageously, this may produce product (compound (III)) in greater than 50% ee, for instance greater than 60% ee. Introducing the chirality at this stage allows the processes hereinbefore described to be effected, thereby circumventing other methods for introducing the chirality (e.g. using chiral 3-hydroxy-piperidine) and circumventing the undesired Mitsunobu reaction prior disclosed in a process for preparing ibrutinib.

Compounds of formula (III), or protected derivatives thereof may be prepared by reaction of a compound of formula (VI),

(VI)

or a derivative thereof, wherein R$^1$ is as hereinbefore defined, with a compound of formula (VII),

R$^2$—N(H)—NH$_2$         (VII)

wherein R$^2$ is hydrogen or a suitable nitrogen protecting group (which may be subsequently removed), which may also be referred to as an aspect of the invention. This aspect of the invention may be conducted under standard dehydration reaction conditions optionally in the presence of a suitable solvent.

In general, the protection and deprotection of functional groups may take place before or after any of the reaction steps described hereinbefore.

Protecting groups may be removed in accordance with techniques which are well known to those skilled in the art and as described hereinafter.

The use of protecting groups is described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

The following scheme (which may have its individual numbering, as may the experimental section) provides a non-limiting example of various processes of the invention:

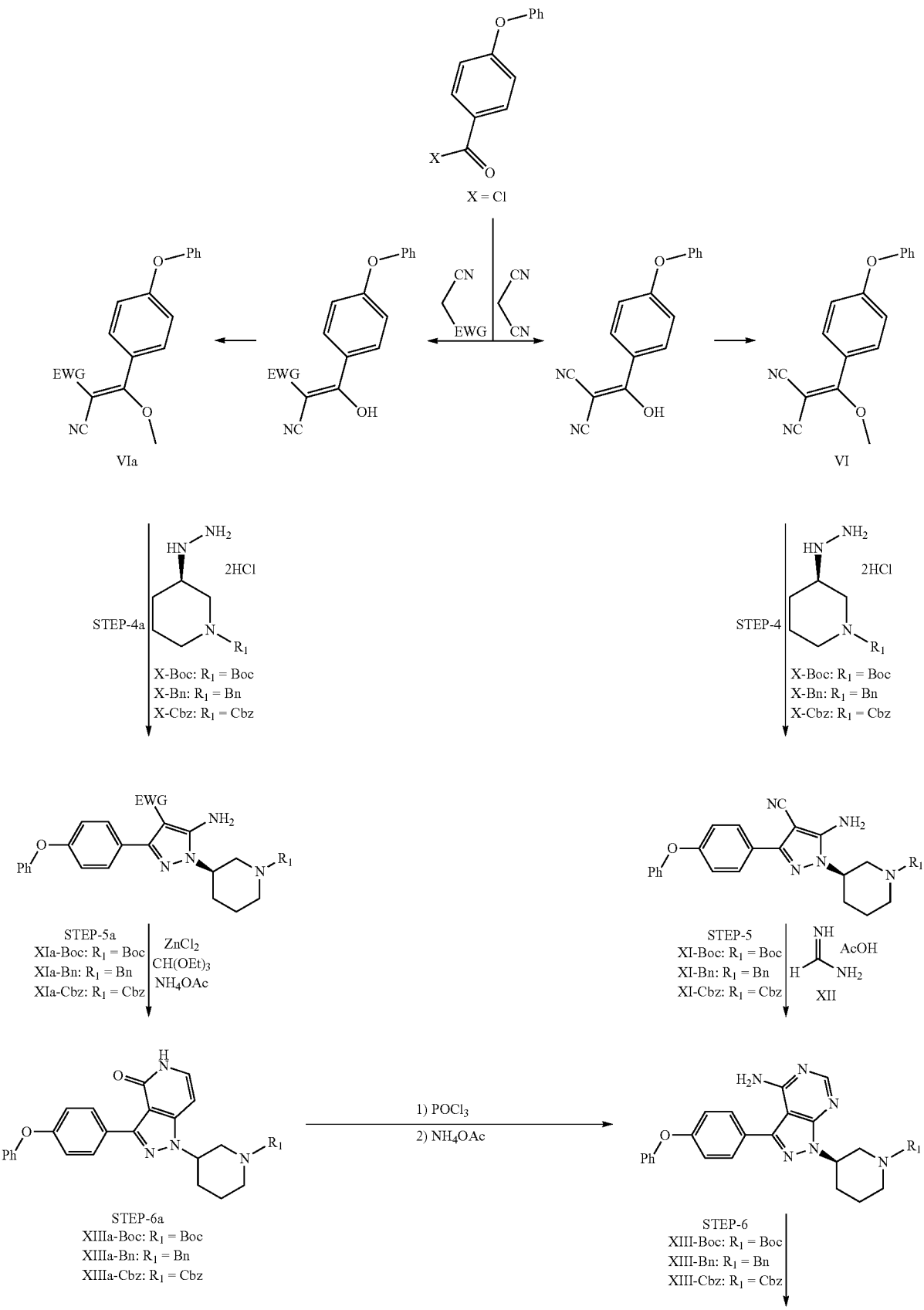

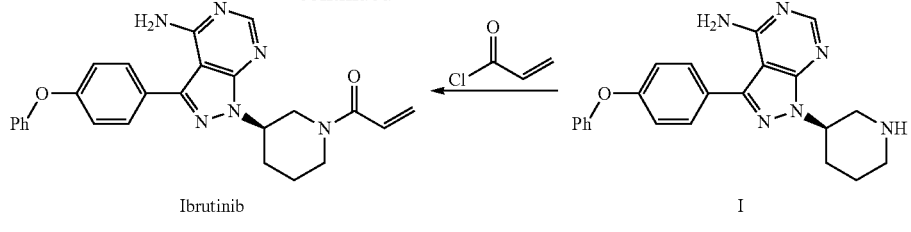

Ibrutinib

EWG = —CO₂Et, CONH₂

I

For instance, for compounds of formula (II) in which $X^1$ represents an alkoxy leaving group —$OR^{3a}$ (or sulfonate), then such a compound may be prepared by alkylation (e.g. methylation) (or appropriate sulfonylation) of a compound corresponding to a compound of formula (II) but in which —$OR^{3a}$ represents —OH. Conversion of the —OH to other suitable leaving groups (e.g. to halo) may also be effected.

Compounds corresponding to formula (II) but in which —$OR^{3a}$ represents —OH may be prepared by reaction of a compound of formula (VIII),

(VIII)

wherein $X^{1a}$ represents a suitable leaving group (e.g. chloro) and $R^{2a}$ is as hereinbefore defined, with a compound of formula (IX),

(IX)

wherein $R^{1a}$ is as hereinbefore defined, under suitable reaction conditions.

Some compounds described herein may be novel themselves, and hence in a further aspect of the invention, there is provided:
   a compound of formula (I) or a derivative thereof
   a compound of formula (III) or a derivative thereof, for instance in at least greater than 50% ee
   a compound of formula (II), (IV) or (IVA) or a derivative thereof.

In an embodiment of the invention, there is provided a process for the preparation of ibrutinib:

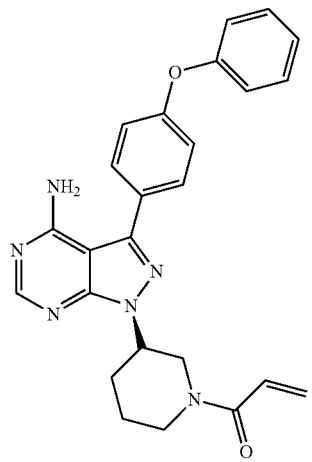

which process comprises a process as defined herein, followed by conversion to ibrutinib, for example:
   a process for the preparation of a compound of formula (I) as herein described, followed by conversion to ibrutinib a process for the preparation of a compound of formula (IV) or (IVA) as herein described, followed by conversion to ibrutinib, for example by deprotection (i.e. removal of the $R^1$ group) followed by acylation with acryl chloride a process for the preparation of a compound of formula (III) as hereinbefore described, followed by conversion to ibrutinib, for example in accordance with the procedures described herein Hence, there is also provided the use of certain compounds (e.g. the use of a compound of formula (I), (IV), (IVA) and/or (III)) as intermediates in the preparation of ibrutinib.

There is then further provided a process for the preparation of a pharmaceutical formulation comprising ibrutinib, which process comprises bringing into association ibrutinib (or a pharmaceutically acceptable salt thereof), which is prepared in accordance with the processes described hereinbefore, with (a) pharmaceutically acceptable excipient(s), adjuvant(s), diluents(s) and/or carrier(s).

In general, the processes described herein, may have the advantage that the compounds prepared may be produced in a manner that utilises fewer reagents and/or solvents, and/or requires fewer reaction steps (e.g. distinct/separate reaction steps) compared to processes disclosed in the prior art.

The process of the invention may also have the advantage that the compound(s) prepared is/are produced in higher yield, in higher purity, in higher selectivity (e.g. higher regioselectivity), in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art. Furthermore, there may be several environmental benefits of the process of the invention.

EXAMPLES

The following examples are intended to illustrate the present invention and should not be construed as a limitation of the scope of the present invention.

Experimental Section

1 Prepare I from XI with Cbz Protecting Group

The synthesis route from XIV-Cbz to I has been performed in the laboratory with the total yield of ~50%. Structure of I from this route has been confirmed by comparing HPLC, HNMR and CNMR with reference standard I.

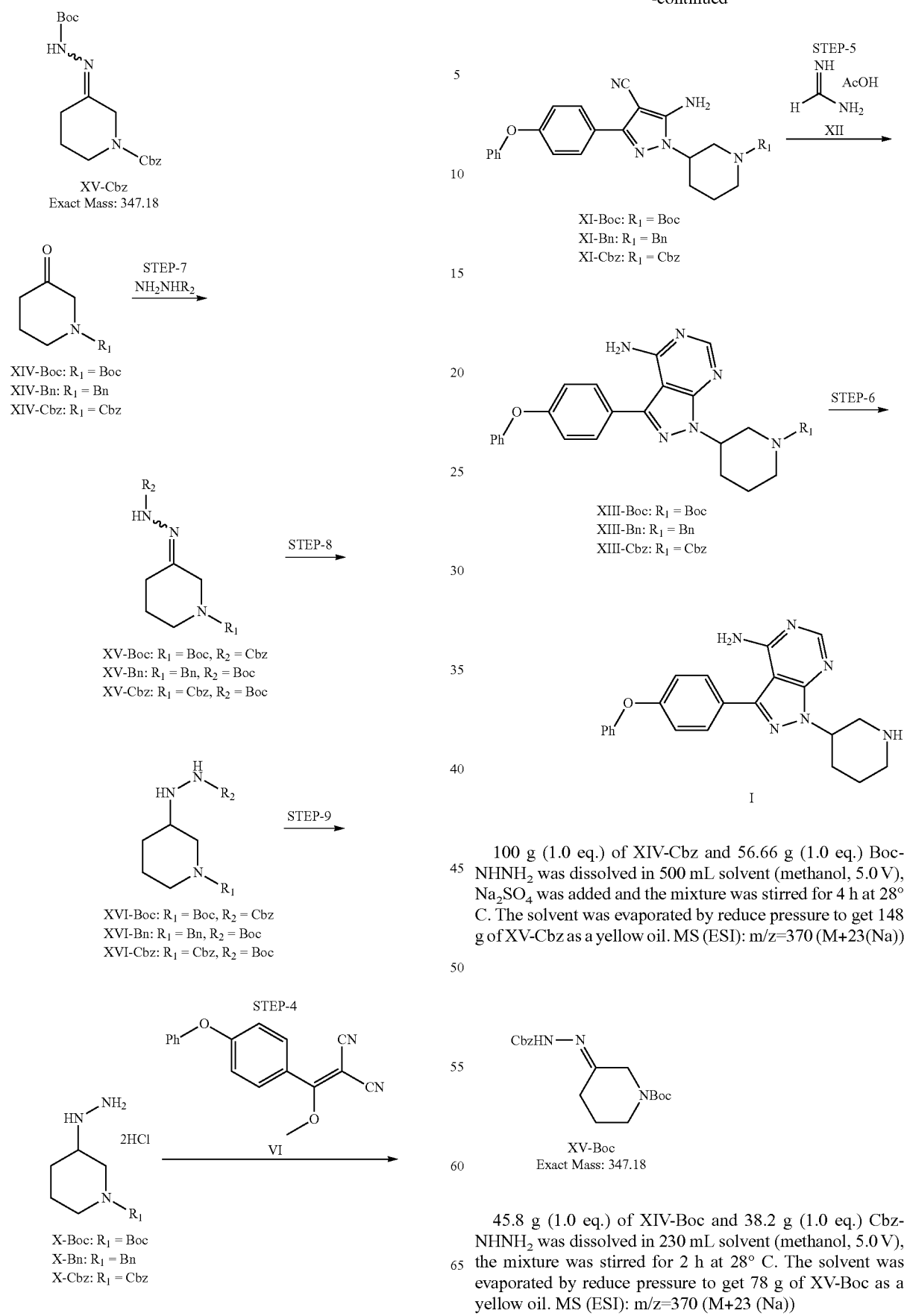

100 g (1.0 eq.) of XIV-Cbz and 56.66 g (1.0 eq.) Boc-NHNH$_2$ was dissolved in 500 mL solvent (methanol, 5.0 V), Na$_2$SO$_4$ was added and the mixture was stirred for 4 h at 28° C. The solvent was evaporated by reduce pressure to get 148 g of XV-Cbz as a yellow oil. MS (ESI): m/z=370 (M+23(Na))

45.8 g (1.0 eq.) of XIV-Boc and 38.2 g (1.0 eq.) Cbz-NHNH$_2$ was dissolved in 230 mL solvent (methanol, 5.0 V), the mixture was stirred for 2 h at 28° C. The solvent was evaporated by reduce pressure to get 78 g of XV-Boc as a yellow oil. MS (ESI): m/z=370 (M+23 (Na))

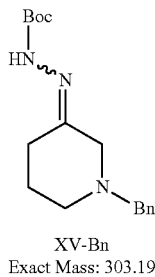

XV-Bn
Exact Mass: 303.19

100 g (1.0 eq.) of XIV-Bn.HCl.H₂O/Bn and 54.22 g (1.0 eq.) Boc-NHNH₂ was dissolved in 500 mL solvent (methanol, 5.0V), Na₂SO₄ was added and the mixture was stirred for 2 h at 25° C. The solvent was evaporated by reduce pressure to get 122 g of XV-Bn as orange foam. MS (ESI): m/z=304 (M+1)

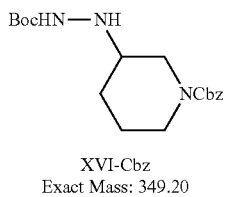 [SMILES: CC(C)(C)OC(=O)NNC1CCCN(C(=O)OCc2ccccc2)C1]

XVI-Cbz
Exact Mass: 349.20

33.11 g (1.0 eq) of XV-Cbz was dissolved in 160 mL of MeOH, cool 5° C. and stirred under nitrogen. 2.0 eq. NaBH₃CN was then added to the reaction mixture. Then, 1.0 eq of AcOH was added dropwise and stirred at 5° C. under nitrogen for 3 h. The reaction mixture was stirred for another 3.5 h at 25° C., cooled to 10° C., and then saturated aq.NH4Cl was added dropwise until pH~6. (A lot of white solid separated out). The mixture was filtered and the solid washed with H₂O. The cake was dried under vacuum at 45-50° C. for 16 hrs and isolated in 81.1% yield. MS (ESI): m/z=372 (M+23 (Na))

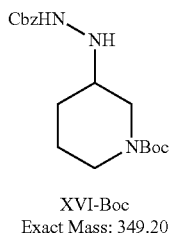 [SMILES: CC(C)(C)OC(=O)N1CCCC(NNC(=O)OCc2ccccc2)C1]

XVI-Boc
Exact Mass: 349.20

28.4 g (1.0 eq) of XV-BOC was dissolved in 145 mL of THF and 30 mL of MeOH, cool 5° C. and stirred under nitrogen. 6.18 g (2.0 eq) of NaBH₄ was then added to the reaction mixture and stir at 5° C. under nitrogen for 3 h. It was allowed to stir for another 15 h at 20° C. 15% aq. NH₄Cl was added dropwise until pH~6-7. Then 10V of Ethyl acetate was charged/added into the mixture. The phase was separated, and the aqueous was extracted twice with 8V of ethyl acetate. The organic layers were combined and washed twice with 10V of water. The organic solution was concentrated to 3-4V and then cooled to 0-5° C. PE was added dropwise to crystallize XVI-Boc as white solid. The mixture was filtered and the cake dried under vacuum at 40-45° C. 25 g of XVI-Boc was obtained with 97.54% HPLC purity in the yield of 87.7%.

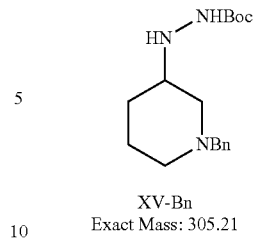

XV-Bn
Exact Mass: 305.21

A MeOH solution of XV-Bn (37.6 g in 130 mL MeOH) was cooled to 5° C. under N₂. 2.0 eq. NaBH₃CN was charged under N₂ keeping the temperature at 5-10° C. 1.0 eq of AcOH was added dropwise at 5-10° C. The mixture was warmed to 25° C. and stirred under N₂ for 16 h. The reaction mixture was cooled to 10° C. Saturated aq.NH4Cl was added dropwise into R1 to pH~6. The mixture was concentrated under vacuum and then aqueous phase was extracted with EA (100 ml*3). The organic phase was concentrated. The mixture was filtered and the filter cake washed with MTBE. The cake was dried under vacuum at 45-50° C. for 16 hrs to get 23 g XVI-Bn as white solid 97.9% purity. MS (ESI): m/z=306 (M+1)

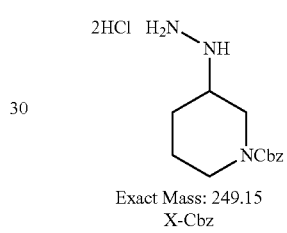

Exact Mass: 249.15
X-Cbz 16.12 g (1.0 eq.) XVI-Cbz was charged with 80 mL of methanol. 92.2 mL MeOH solution of HCl (4M) was charged and stirred for 3 h at 28° C. MeOH was switched to EtOAc (a lot of white solid separated out). The solid was filtered under N₂ protection. The filter cake was dried under vacuum at 35-40° C. for 16 hrs to result in 11.9 g (80.2% Yield) with a purity of 94.97%. (ESI): m/z=249.9 (M+1)

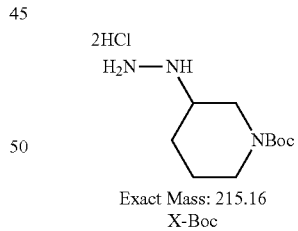

Exact Mass: 215.16
X-Boc

Pd(OH)₂/C was used as catalyst and 2.0 eq HCl (2M MeOH solution) was added to inhibit the generation of a dimmer by-product. Form LCMS, a strong MS signal of X-Boc could be found. After the workup, 3.9 g of X-Boc was obtained as foam in the yield of 79.6%.

Procedure: Charge 6.0 g (1.0 eq.) of XVI-Boc with 90 mL (15.0 V.) Methanol, then charge 3.61 g (0.30 eq.) Pd(OH)₂/C with 34.36 mL (2.0 eq) of MeOH solution of HCl (1M), stir for 1 h at 28° C. under N₂. Swich the solvent to EtOAc to separate the product out. Transfer the mother liquor out and dry the residue under vacuum to get 3.9 g of X-Boc as white foam (79.6% Yield). (ESI): m/z=216.0 (M+1)

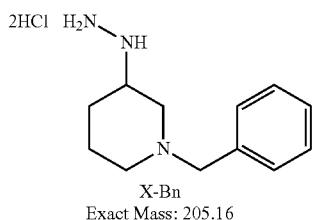 [SMILES: "2HCl" ; NNC1CCCN(Cc2ccccc2)C1]

X-Bn
Exact Mass: 205.16

Charge 20 g (1.0 eq) of XVI-Bn under N₂, add 11 eq. HCl MeOH solution (4M) into R1 under N₂ at 20-25° C. and stir at 50° C. for 2 h. Switch the solvent to EtOAc and then a lot of white solid separated out. Filter the mixture under N₂ protection. The solid was dried under vacuum at 45-50° C. to yield 14 g of X-Bn (76.9% Yield).

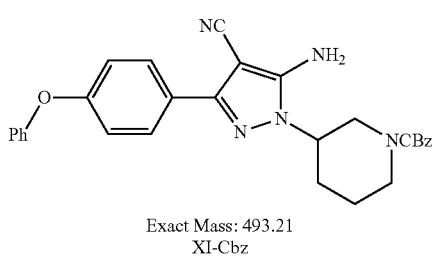

Exact Mass: 493.21
XI-Cbz

Charge 4.29 g (1.0 eq.) of VI under N₂ with 60 mL (13 V.) ethanol and 43 ml (10V) of water. Cool the mixture to 5° C. Add X-Cbz in three portions at 5-10° C. under N₂. Add dropwise 3.15 g (2.0.eq.) NEt₃ at 5-10° C. Warm to 25° C. under N2 and stir for 1 h at 25° C. (solid separate out). Add dropwise 17V H₂O into the reaction mixture at 25° C. Cool the reaction mixture 0-5° C. and stir for 1 h. Filter the mixture. The cake was dried under vacuum at 40-45° C. to result in 7.79 g (100% Yield) with a purity of 99.81% (ESI): m/z=494.1 (M+1)

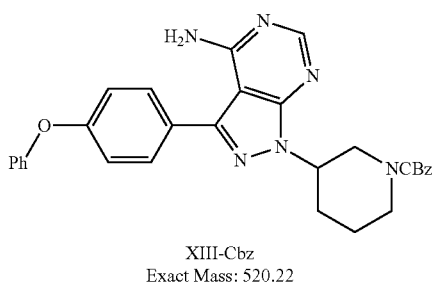

XIII-Cbz
Exact Mass: 520.22

3 g (1.0 eq) of XI-Cbz was mixed with 9.5 g (15.0 eq) of formamidine acetate and 40 mL (13V) C₂H₅OC₂H₄OH (degassed), the reaction mixture was stirred at 120° C. for 6 hrs, Cool the reaction mixture to r.t. Add dropwise H2O (13V) and EA (15V). Separate the mixture and extract the aqueous phase with EA fro twice. Combine the organic phase and wash it with H₂O twice. Evaporate solvent under vacuum to get crude XIII-Cbz as yellow oil in 97.9% purity. (ESI): m/z=521.4 (M+1)

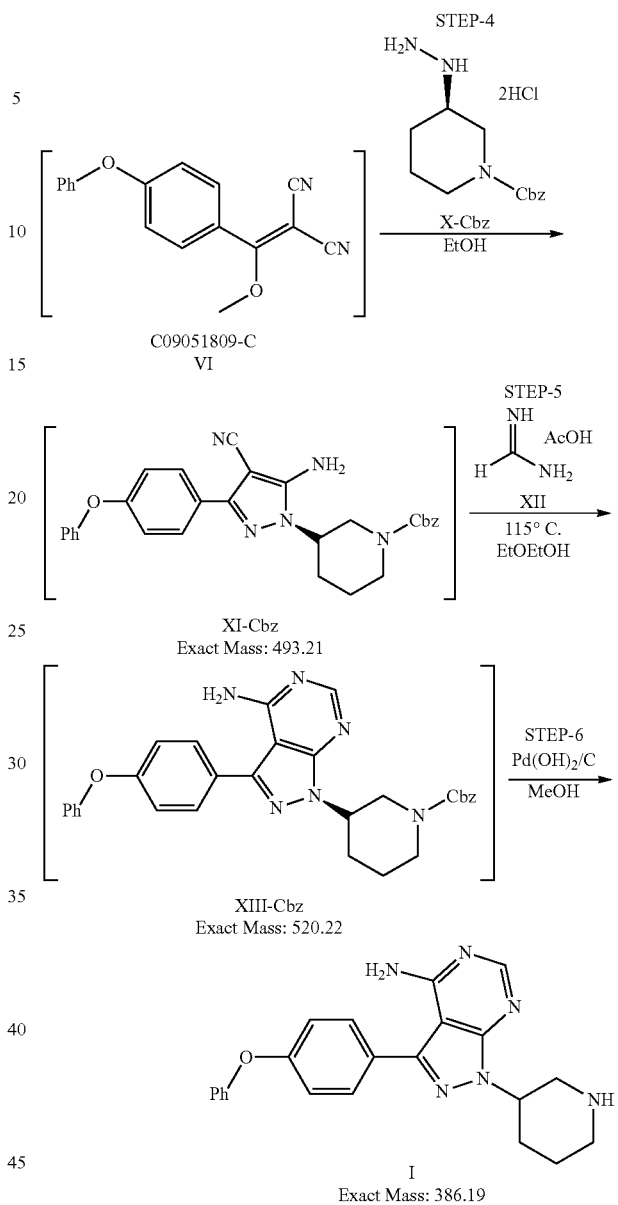

Telescope preparation of I from VI was carried out. In step-4, conversion of VI was 100% and XI-Cbz was generated with 99.8% area percent. In step-5, conversion of XI-Cbz was 97.7% and XIII-Cbz was generated with 94.2% area percent. In step-6, conversion of XIII-Cbz was 100% and I was obtained with 92.5% HPLC area percent.

Procedure: Charge 4.29 g (1.0 eq.) VI under N2 with 10 mL (16.6 V.) ethanol and 6 ml (10V.) Cool R1 to 5-10° C. Add 0.7 g (1.0.eq.) X-Cbz solution in water was added drop-wise over 15 min at 5-10° C. Add 0.45 g (2.0.eq.) NEt₃ drop-wise over 5 min at 5-10° C. Warm to 2030° C. under N₂ and stir R1 for 1 h at 2030° C. Add 10V EA and then 10V H2O into the reaction mixture. Separate the mixture and extract the aqueous phase with 10V EA twice. Combine the organic phase and wash with 10V H2O. Switch the solvent to 13V EtOEtOH. Add 15 eq formamidine acetate into the mixture. Heat to 120° C. and stir for 5 hrs at 120° C. Cool the mixture to r.t. and add 15V EA and 15V H2O into the mixture. Separate the mixture and extract the aqueous phase with 10V EA twice. Combine the organic phase and wash with 10V H2O twice. Switch the solvent to 10V MeOH. Add Pd(OH2)/C (0.3 eq) and stir the mixture at 55-60° C. under 3 Bar H₂. Filter the reaction mixture and wash the cake with MeOH. Combine the MeOH solution of crude I and concentrate to 2-3VAdd dropwise H2O (5-6V) into the MeOH solution (a lot of off-white solid separated out). Filter the mixture and wash the cake with MeOH/H2O (1V/1V). The solid was dried under vacuum at 40-45° C. to obtain I in 80% yield (over 3 steps) in 92.5% purity.

By comparing the HPLC, HNMR and CNMR of I with a reference of that compound e.g. known from the art (or derivatised therefrom), it could be concluded that I that is prepared by this synthesis had the same HPLC retention time, same HNMR and CNMR. Therefore, this synthesis route from SM-Cbz to I is an available working route.

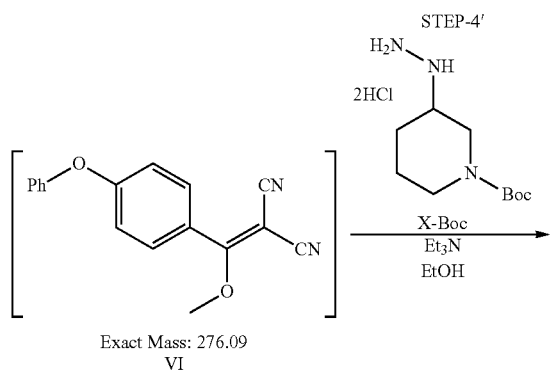

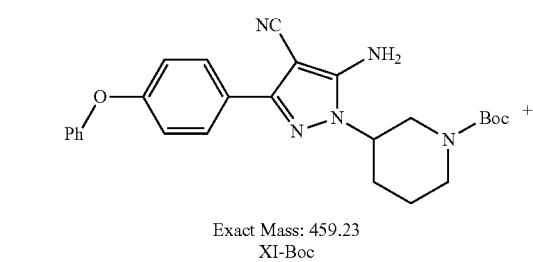

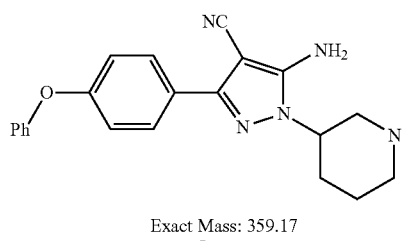

Charge 0.41 g (1.0 eq.) of VI (in THF solution). Dissolve 0.32 g (1.0 eq.) of X-Boc in EtOH (2V)/H2O (0.5 mL, 1.5V)/Et3N (3.0 eq). Add drop-wise X-Boc to R1 at 5-10° C. Warm to 25° C. under N2 and stir R1 for 1 h at 25° C. Add water (10V) drop-wise at 5-10° C. Concentrate the mixture under vacuum and extract it with ethyl acetate (20 m*3). Wash the organic phase with H2O. Evaporate solvent under vacuum to get crude XI-Boc as yellow oil. The de-Boc compound, Imp-A, was generated as the main product. XI-Boc was obtained in 29% yield with 96% purity by column chromatography

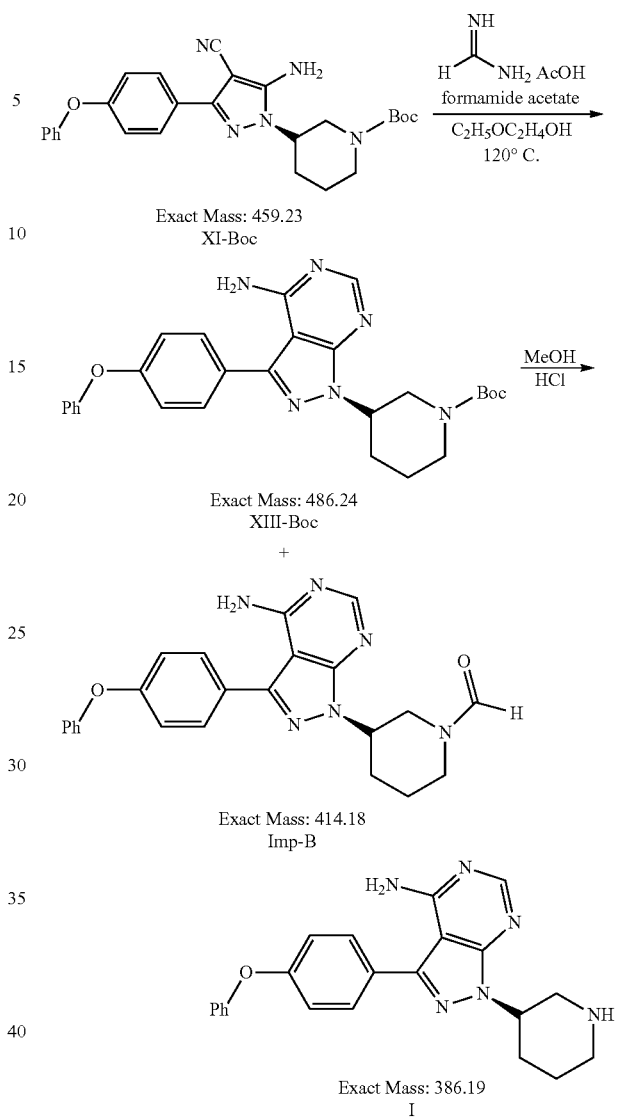

Charge XI-Boc (0.3 g, 1.0 eq.) at r.t under N2. Charge formamidine acetate (15 eq) into R1 under N2. Charge C₂H₅₀C₂H₄OH (13V) into R1 under N2. Heat to 120° C. (inter temp) and stir the mixture at 120° C. for 8 hrs. In this reaction mixture, 4.3% of Imp-B also could be observed. Cool the reaction mixture to r.t. Add dropwise H2O (40 mL, 13V) and EA (15V). Separate the mixture and extract the aqueous phase with EA twice. Combine the organic phase and switch the solvent to MeOH. Add HCl (10 eq, MeOH solution) into the mixture. Heat to 50° C. and stir for 3 hrs. Cool to r.t, concentrate the reaction mixture to 2-3 mL. Add 3 mL H2O and then add dropwise 30% aq. NaOH to adjust pH to 10. Filter the mixture and dry the cake under vacuum at 45° C. I could be isolated by crystallization form MeOH/H₂O with 95.6% purity in the total yield of 87.3%

By comparing the HPLC, HNMR and CNMR of I with a reference of that compound e.g. known from the art (or derivatised therefrom), it could be concluded that I that is prepared by this synthesis had the same HPLC retention time, same HNMR and CNMR. Therefore, this synthesis route from SM-Boc to I is an available working route.

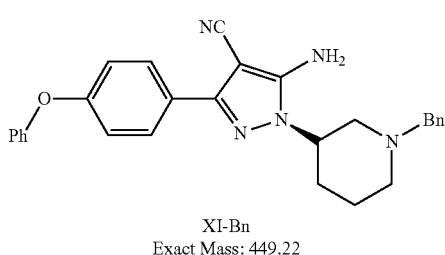

XI-Bn
Exact Mass: 449.22

Charge 0.496 g (1.0 eq.) of VI under N2 with 4 mL (8V.) ethanol. Cool the mixture to 5° C. Add X-Bn (dissolve in 5V EtOH and 10V H$_2$O) in three portions at 5-10° C. under N2. Add dropwise 0.51 g (2.0.eq.) NEt$_3$ at 5-10° C. Warm to 25-30° C. under N2 and stir for 1 h at 25-30° C. (solid separate out). Add dropwise 17V H$_2$O into the reaction mixture at 25° C. Cool the reaction mixture 0-5° C. and stir for 1 h. Filter the mixture. The cake was dried under vacuum at 40-45° C. to yield 0.65 g of XI-Bn (80% Yield) with 94.03% purity. (ESI): m/z=450 (M+1)

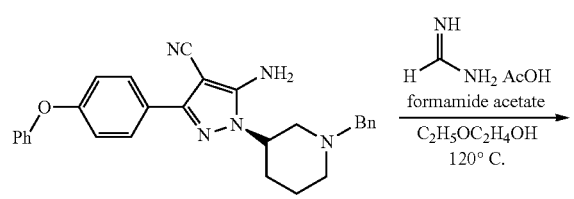

Exact Mass: 449.22
XI-Bn

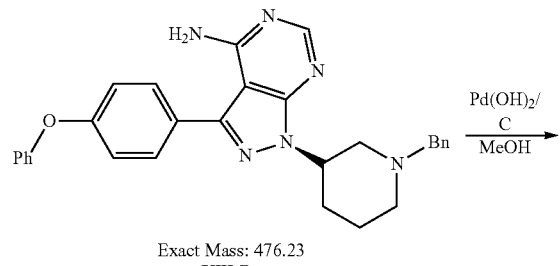

Exact Mass: 476.23
XIII-Bn

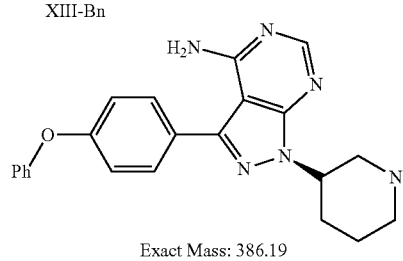

Exact Mass: 386.19
I

One batch to prepare XIII-Bn was carried out from 1.72 g XI-Bn. In the first ring closure step, Conversion of XI-Bn was 100% and XIII-Bn was generated with 99.12% LCMS purity. Even been stirred for 21 hrs at 120° C., no decomposition could be observed. In the second step, we tried two conditions. One added 2 eq of HCl (4M MeOH solution) and the other one was without HCl. The batch adding HCl was faster than the other one. However, conversion of XIII-Bn was only 20%. Procedure: Charge XI-Bn at r.t with formamidine acetate (15 eq) and C$_2$H$_5$OC$_2$H$_4$OH (13V) under N2. Heat to 120° C. and stir the mixture at 120° C. for 8 hrs. Cool the reaction mixture to r.t. Add dropwise H2O (13V) and EA (10V). Separate the mixture and extract the aqueous phase with 10V EA for twice. Combine the organic phase and wash it with 10V H2O for three times. Switch the solvent to MeOH from EA. Charge 0.1 eq Pd(OH)$_2$/C and 2 eq HCl (4M MeOH solution). Heat to 45-50° C. Stir the mixture in R$^2$ at 40-50° C. The desired product was obtained from this procedure. (ESI): m/z=387.0 (M+1)

Example

Pharmaceutical Formulation

Ibrutinib may be formulated into a pharmaceutically acceptable formulation using standard procedures.

For example, there is provided a process for preparing a pharmaceutical formulation comprising ibrutinib, or a derivative thereof, which process is characterised in that it includes as a process step a process as hereinbefore defined. The skilled person will know what such pharmaceutical formulations will comprise/consist of (e.g. a mixture of active ingredient (i.e. ibrutinib or derivative thereof) and pharmaceutically acceptable excipient, adjuvant, diluent and/or carrier).

There is further provided a process for the preparation of a pharmaceutical formulation comprising ibrutinib (or a derivative thereof), which process comprises bringing into association ibrutinib, or a pharmaceutically acceptable salt thereof (which may be formed by a process as hereinbefore described), with (a) pharmaceutically acceptable excipient(s), adjuvant(s), diluent(s) and/or carrier(s).

The invention claimed is:
1. A process for the preparation of a compound of formula (IVA),

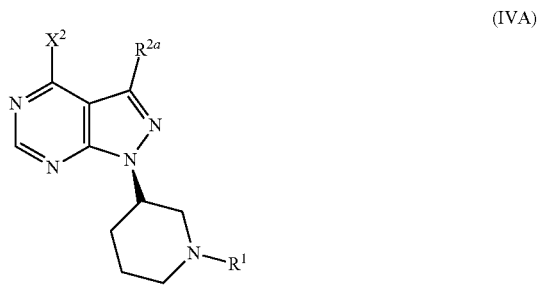

or a salt, or solvate thereof;
wherein the process comprises conversion of a compound of formula (I):

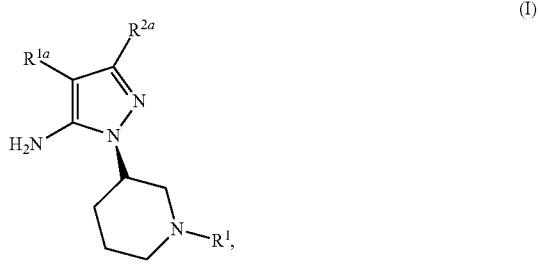

or a salt, or solvate thereof; to the compound of formula (IVA), or a salt, or solvate thereof;

wherein X² represents —NH₂;

R¹ represents a nitrogen protecting group;

R²ᵃ represents phenyl substituted at the 4-position with halo or —O—R²ᵇ; and

R²ᵇ represents hydrogen or phenyl;

and wherein the conversion comprises either a reaction of the compound of formula (I), or a salt, or solvate thereof; wherein R¹ᵃ is —CN; with (i) formamide (HCONH₂);

(ii) formamidine or a salt thereof;

(iii) alkyl formimidate, or a salt thereof; or (iv) ethylorthoformate followed by ammonium acetate;

or a) a reaction of the compound of formula (I), or a salt, or solvate thereof; wherein R¹ᵃ is —C(O)OR¹ᵇ or —C(O)N(R¹ᶜ)(R¹ᵈ); and R¹ᵇ, R¹ᶜ and R¹ᵈ each independently represent $C_{1-6}$ alkyl, aryl or heteroaryl; with ethylorthoformate followed by ammonium acetate to form a compound of formula (IVA) wherein X² is OH; and b) reaction of the resulting compound of formula (IVA) wherein X² is OH, with POCl₃ followed by ammonium acetate.

2. The process according to claim 1, wherein the conversion comprises a reaction of the compound of formula (I), wherein R¹ᵃ is —CN; or a salt, or solvate thereof, with formamidine or a formamidine salt.

3. The process according to claim 1; wherein the conversion comprises a reaction of the compound of formula (I), wherein R¹ᵃ is —CN; or a salt, or solvate thereof, with formamidine HCl or formamidine acetate.

4. The process as claimed in claim 3, wherein the reaction is performed at a temperature of below 160° C.

5. A process for the preparation of ibrutinib:

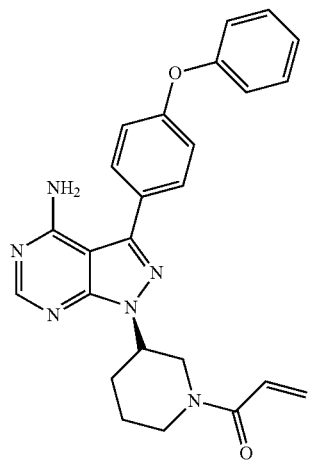

comprising the steps of:

(A) reaction of the compound of formula (XI),

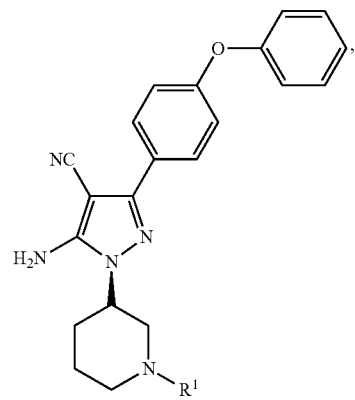

(XI)

or a salt, or solvate thereof; with (i) formamide (HCONH₂);

(ii) formamidine or a salt thereof;

(iii) alkyl formimidate, or a salt thereof; or (iv) ethylorthoformate followed by ammonium acetate;

to form a compound of formula (IV):

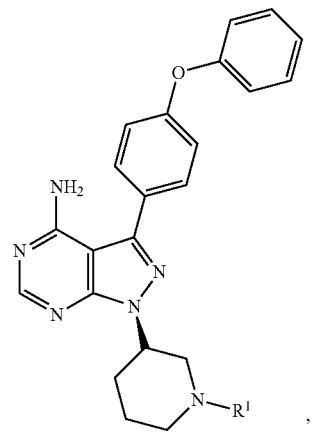

(IV)

or a salt, or solvate thereof, wherein R¹ is a nitrogen protecting group;

(B) deprotection of the compound of formula (IV), or a salt, or solvate thereof, to form the deprotected compound:

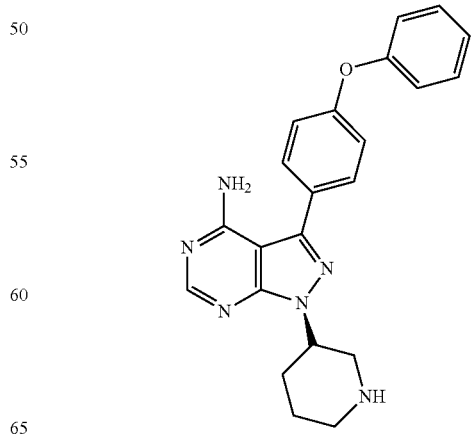

or a salt, or solvate thereof; and (C) acylation of the deprotected compound with acryl chloride to form ibrutinib.

6. The process as claimed in claim 1, wherein the compound of formula (I), or a salt, or solvate thereof, is prepared by a method comprising a reaction of a compound of formula (II),

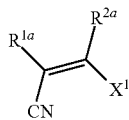
(II)

or a salt, or solvate thereof, with a compound of formula (III),

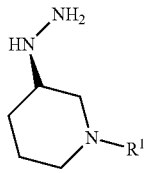
(III)

or a salt, or solvate thereof,
wherein
$R^1$, $R^{1a}$ and $R^{2a}$ are as defined in claim 1,
$X^1$ represents chloro, bromo, iodo, —$OR^{3a}$ or —O—S(O)$_2R^{4a}$,
$R^{3a}$ represents optionally substituted alkyl, and
$R^{4a}$ represents optionally substituted alkyl or aryl.

7. The process as claimed in claim 6, wherein the compound of formula (III) has an ee of greater than 50%.

8. The process as claimed in claim 6, wherein $X^1$ represents —$OCH_3$, —$OCH_2$-phenyl, —$OS(O)_2CF_3$, —$OS(O)_2CH_3$ or —$S(O)_2PhCH_3$.

9. The process as claimed in claim 5, wherein the compound of formula (XI), or a or a salt, or solvate thereof, is prepared by a method comprising a reaction of a compound of formula (II),

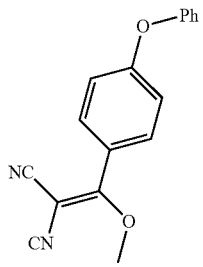
(II)

or a salt, or solvate thereof, with a compound of formula (III),

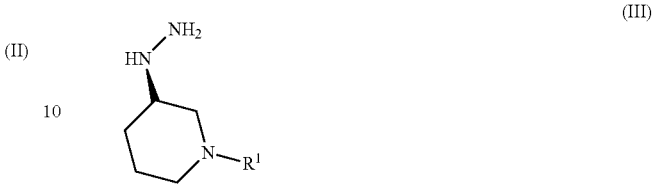
(III)

or a salt, or solvate thereof, wherein $R^1$ is as defined in claim 5.

10. The process as claimed in claim 9, wherein the compound of formula (III) has an ee of greater than 50%.

11. The process as claimed in claim 5, wherein the conversion of the compound of formula (XI), or a salt, or solvate thereof, to the compound of formula (IV), or a salt, or solvate thereof, comprises a reaction of the compound of formula (XI) with formamide ($HCONH_2$).

12. The process as claimed in claim 5, wherein the conversion of the compound of formula (XI), or salt or solvate thereof, to the compound of formula (IV), or a salt, or solvate thereof, comprises a reaction of the compound of formula (XI) with formamidine or a formamidine salt.

13. The process as claimed in claim 5, wherein the conversion of the compound of formula (XI), or a salt, or solvate thereof, to the compound of formula (IV), or a salt, or solvate thereof, comprises a reaction of the compound of formula (XI) with formamidine HCl or formamidine acetate.

14. The process as claimed in claim 13, wherein the reaction is performed at a temperature of below 160° C.

15. The process as claimed in claim 14, wherein the temperature is between 100° C. and 140° C.

16. A process as claimed in claim 5, wherein the conversion of the compound of formula (XI), or a salt, or solvate thereof, to the compound of formula (IV), or a salt, or solvate thereof, comprises a reaction of the compound of formula (XI) with alkyl formimidate, or a salt thereof.

* * * * *